US007872140B2

(12) United States Patent
Kumar et al.

(10) Patent No.: US 7,872,140 B2
(45) Date of Patent: Jan. 18, 2011

(54) BARIUM SALT OF BENZIMIDAZOLE DERIVATIVE

(75) Inventors: Yatendra Kumar, Haryana (IN); Mahavir Singh Khanna, Delhi (IN); Mohan Prasad, Haryana (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 12/467,051

(22) Filed: May 15, 2009

(65) Prior Publication Data

US 2009/0259047 A1 Oct. 15, 2009

Related U.S. Application Data

(62) Division of application No. 10/555,628, filed as application No. PCT/IB2004/001347 on May 3, 2004, now abandoned.

(30) Foreign Application Priority Data

May 5, 2003 (IN) .......................... 665/DEL/2003

(51) Int. Cl.
*C07D 401/12* (2006.01)
(52) U.S. Cl. .................................. 546/273.7
(58) Field of Classification Search ............... 546/273.7
See application file for complete search history.

(56) References Cited

U.S. PATENT DOCUMENTS

| 4,738,974 | A | 4/1988 | Brändström | 514/338 |
|---|---|---|---|---|
| 5,399,700 | A | 3/1995 | Min et al. | 546/271 |
| 5,714,504 | A | 2/1998 | Lindberg et al. | 514/338 |
| 5,900,424 | A | 5/1999 | Källström et al. | 514/338 |
| 5,948,789 | A | 9/1999 | Larsson et al. | 514/299 |
| 6,162,816 | A | 12/2000 | Bohlin et al. | 514/338 |
| 6,262,085 | B1 | 7/2001 | Whittle et al. | 514/338 |
| 6,511,996 | B1 | 1/2003 | Nilsson | 514/338 |
| 7,271,182 | B2 * | 9/2007 | Kamiyama et al. | 514/338 |

FOREIGN PATENT DOCUMENTS

| EP | 1 186 602 | 3/2002 |
|---|---|---|
| EP | 1 306 375 | 5/2003 |
| WO | WO 92/08716 | 5/1992 |
| WO | WO 98/54171 | 12/1998 |
| WO | WO 00/44744 | 8/2000 |
| WO | WO 03/074514 | 9/2003 |
| WO | WO 03/089408 | 10/2003 |

* cited by examiner

*Primary Examiner*—Patricia L Morris
(74) *Attorney, Agent, or Firm*—James DeYonker, Esq.; William D. Hare, Esq.

(57) ABSTRACT

The invention relates to crystalline barium salt of (S)-omeprazole, which is (S)-5-methoxy-2-[[(4-methoxy-3,5-dimethyl-2-pyridinyl)-methyl]sulfinyl]-1H-benzimidazole. The invention also relates to processes for preparing crystalline barium salt of (S)-omeprazole and pharmaceutical compositions that include the crystalline barium salt of (S)-omeprazole so prepared.

10 Claims, 11 Drawing Sheets

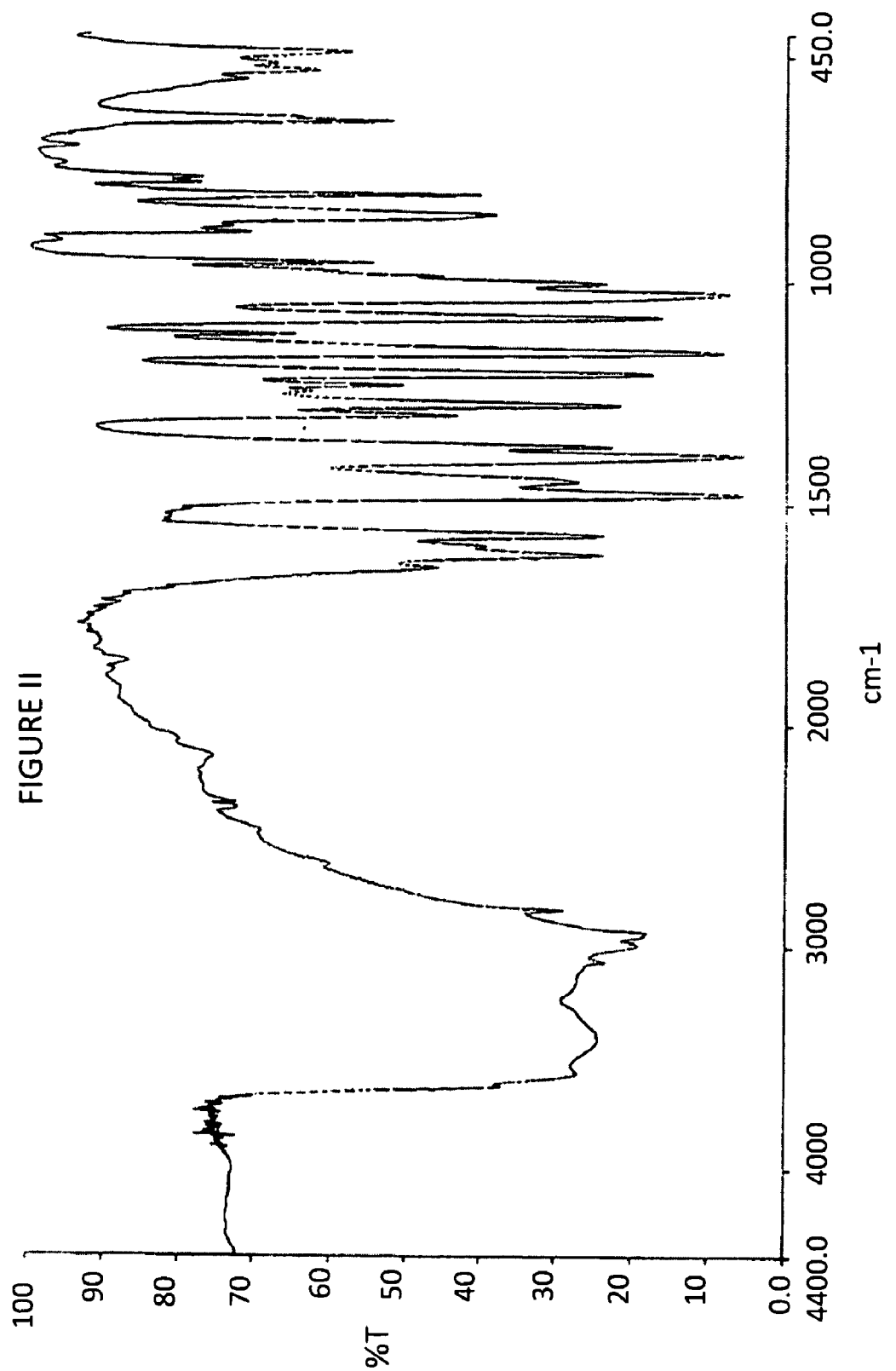
FIGURE II

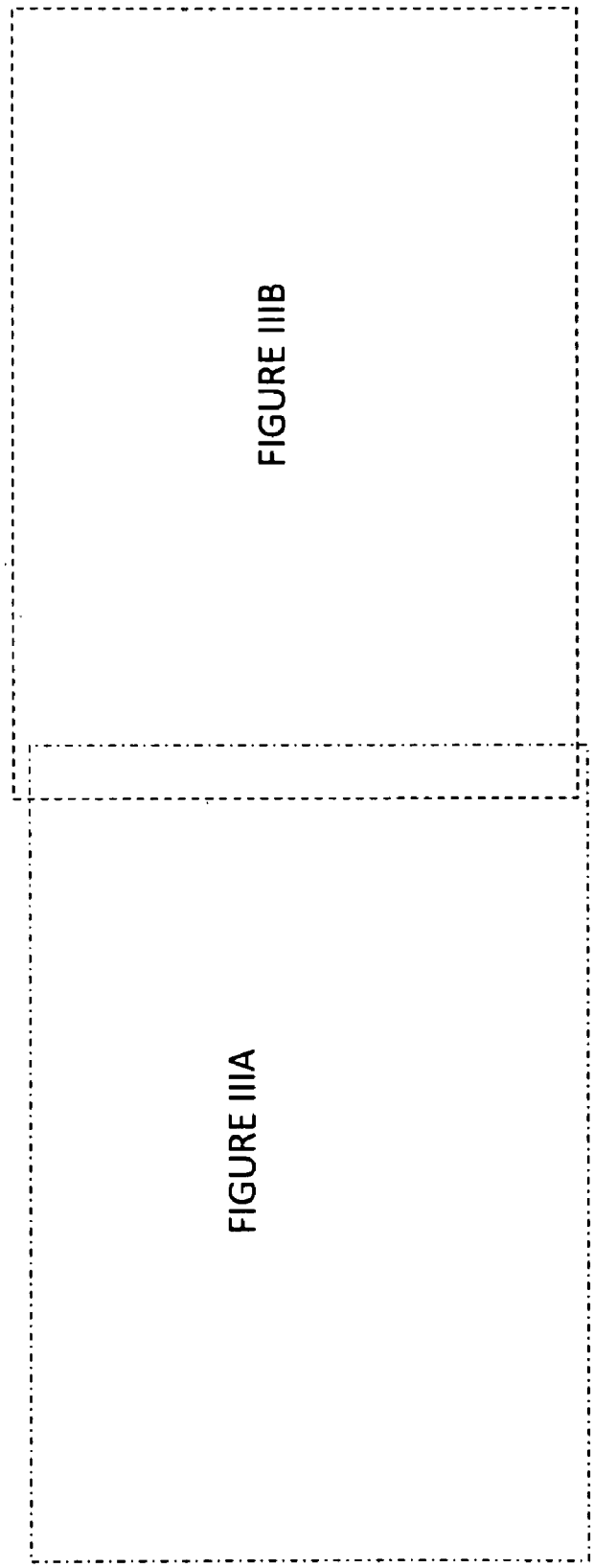

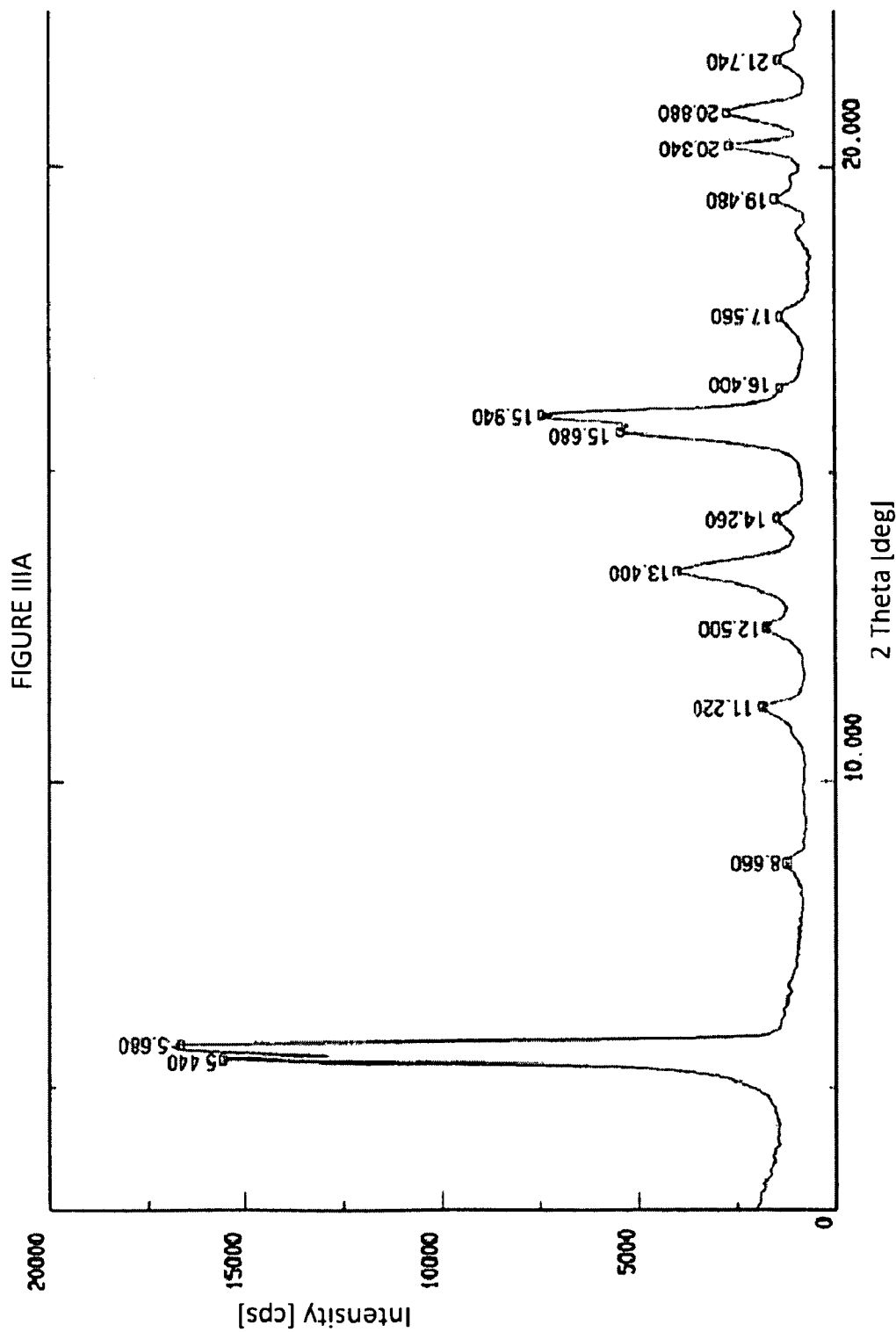
FIGURE IIIA

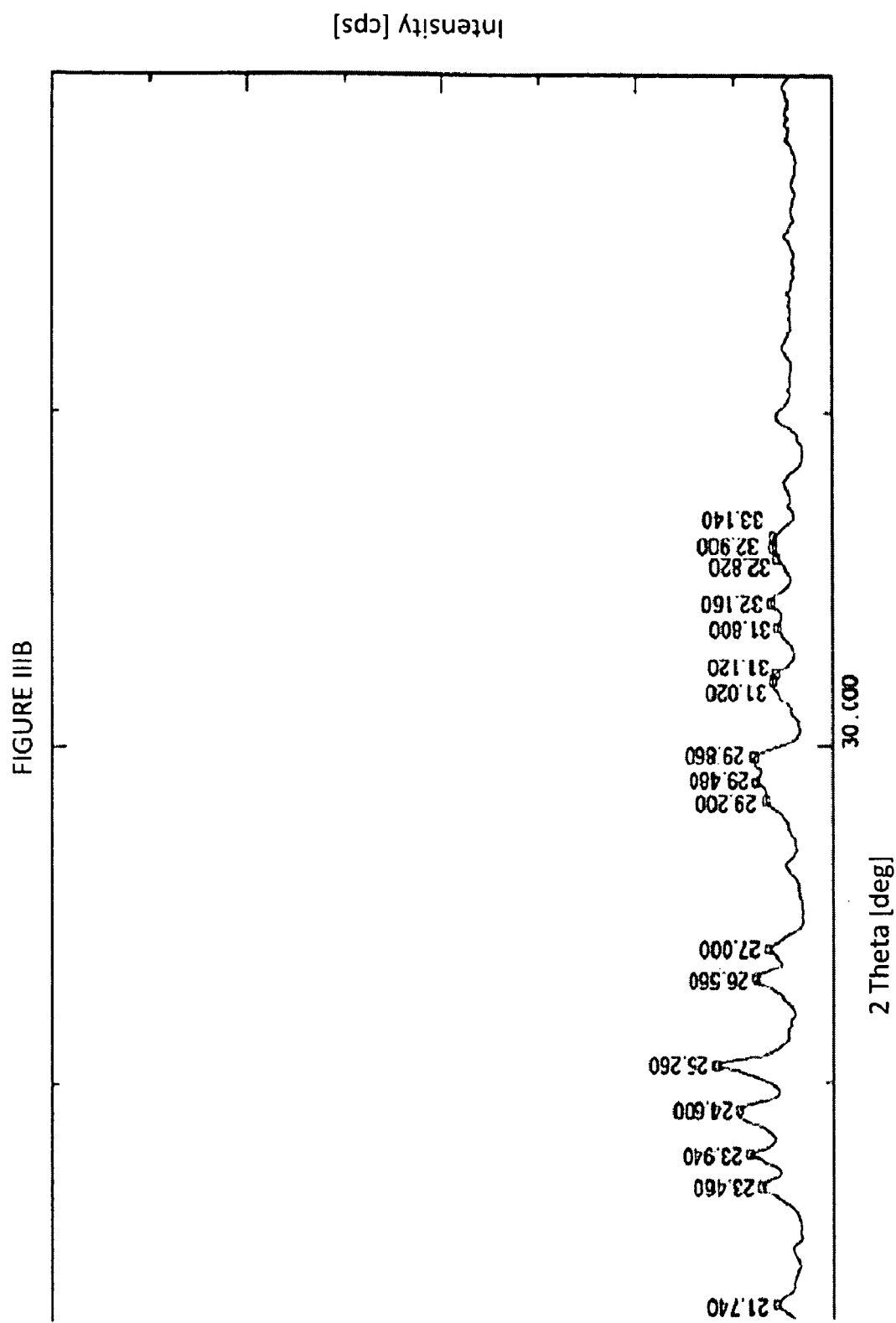
FIGURE IIIB

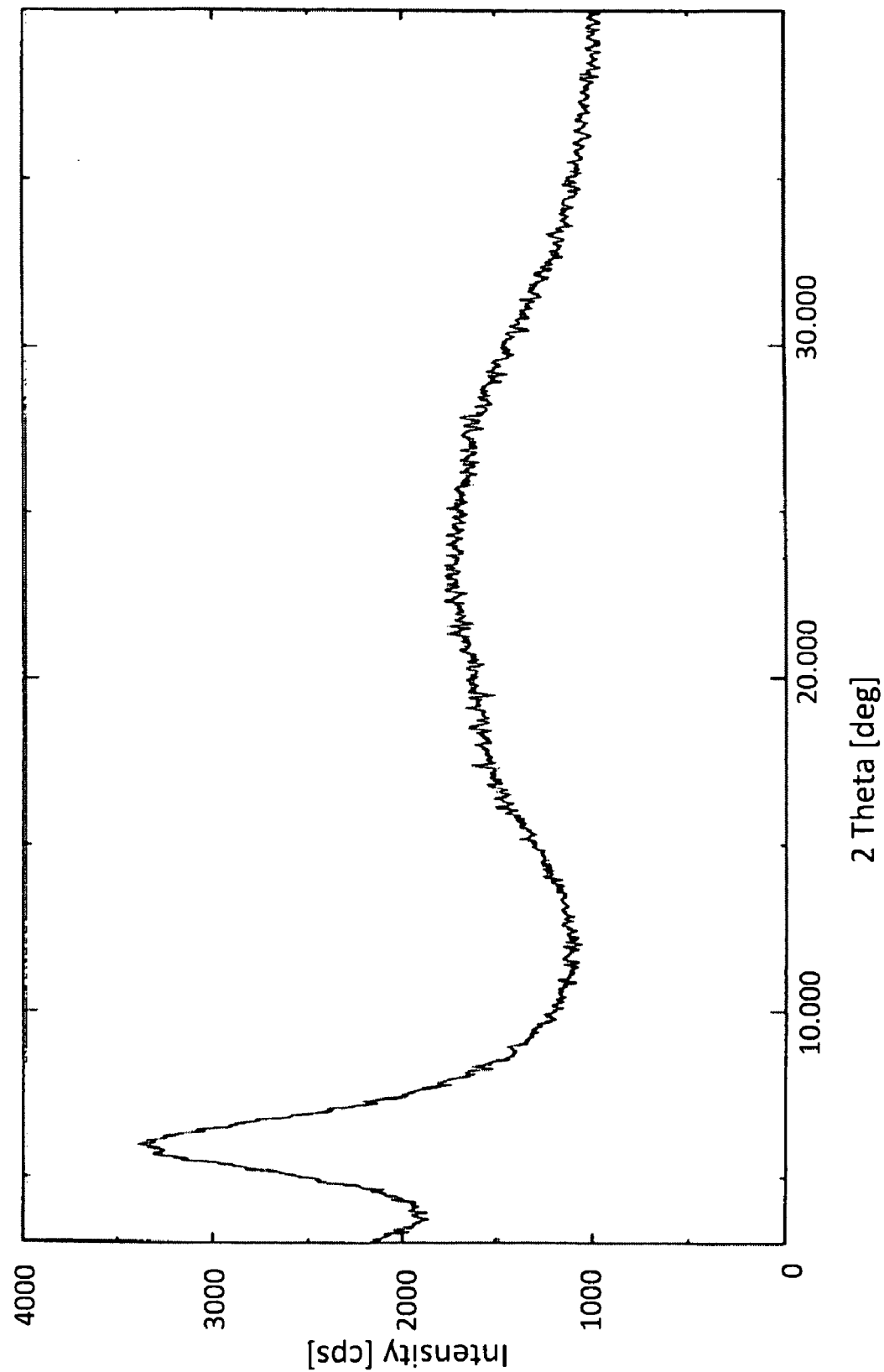
FIGURE IV

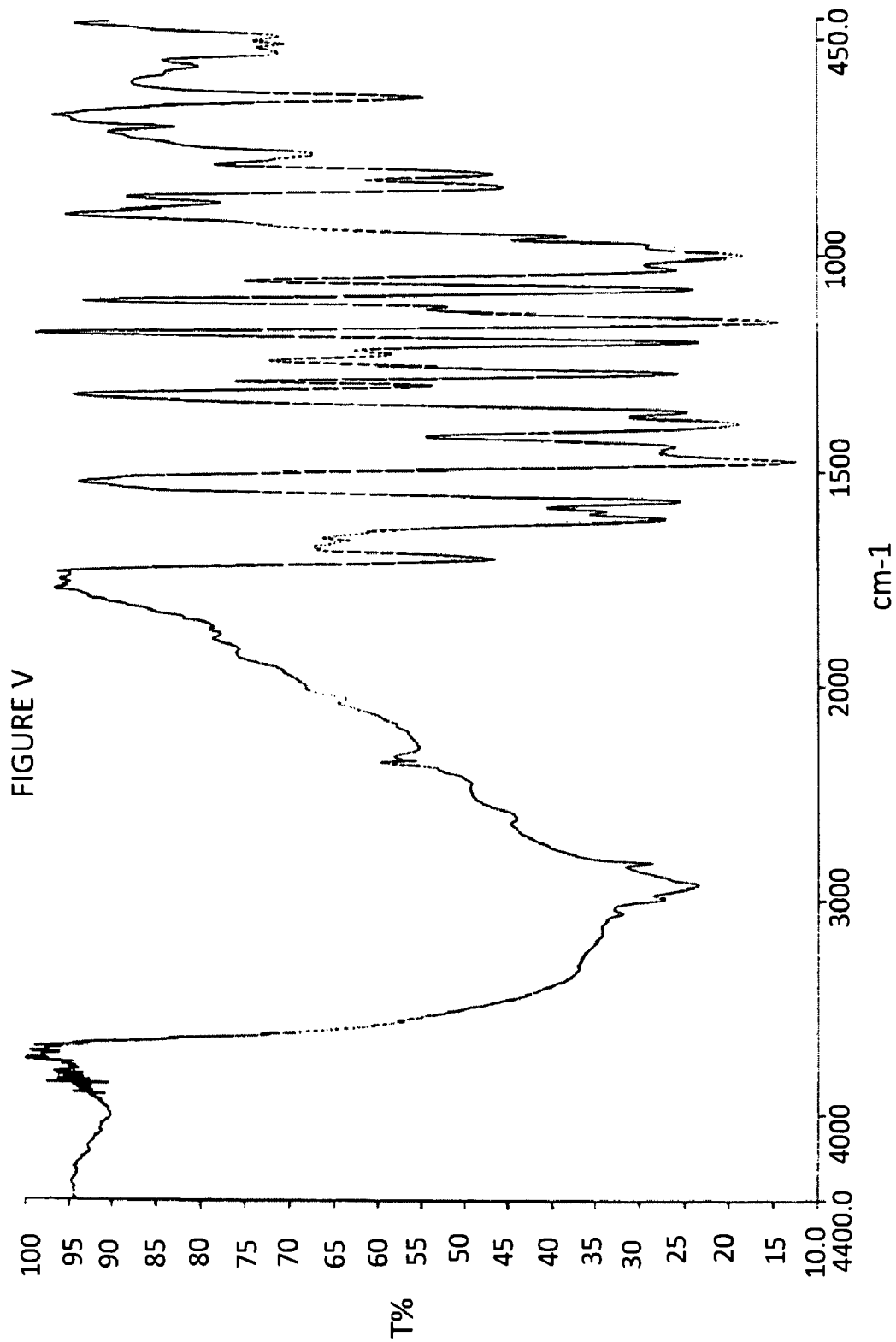
FIGURE V

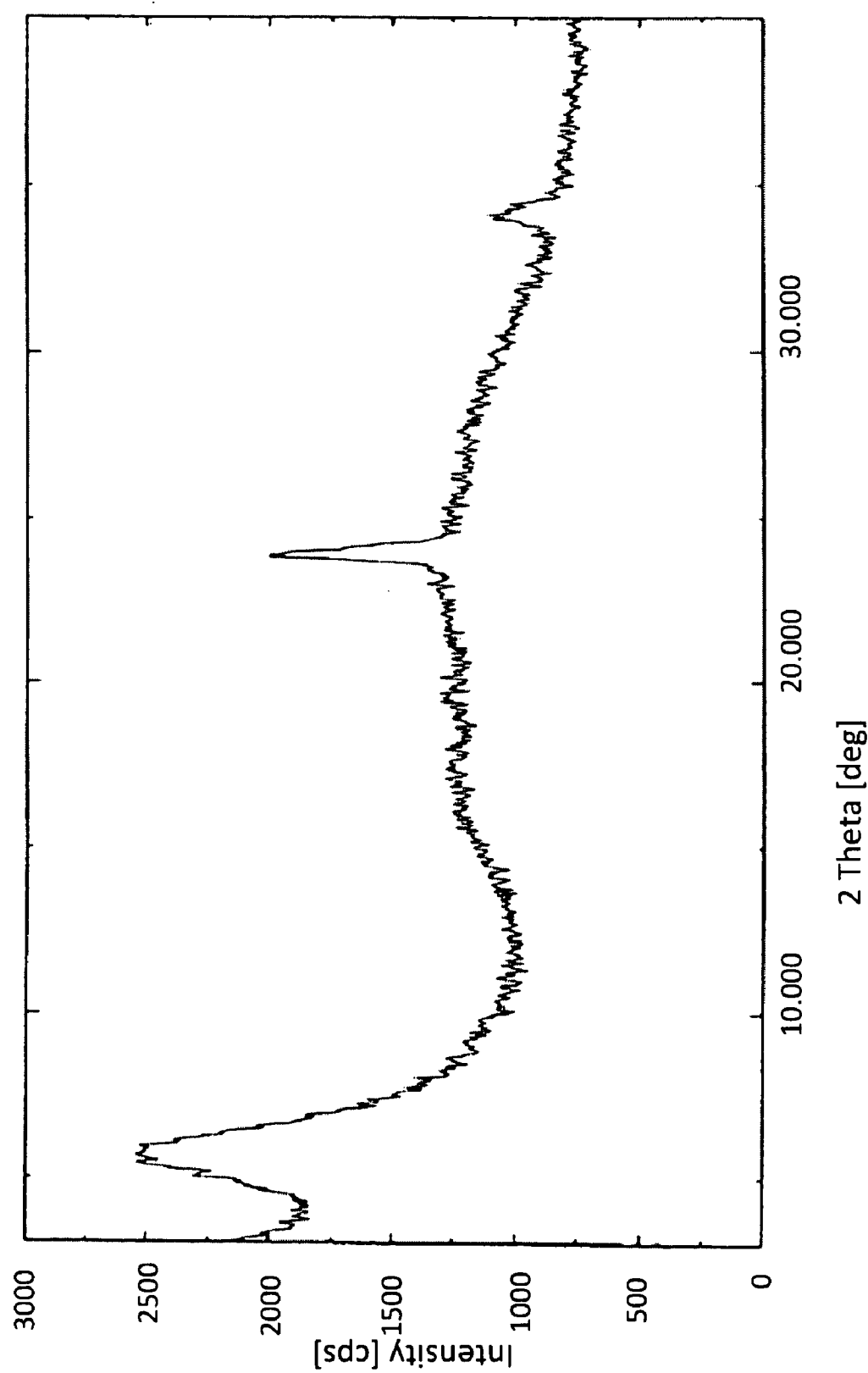

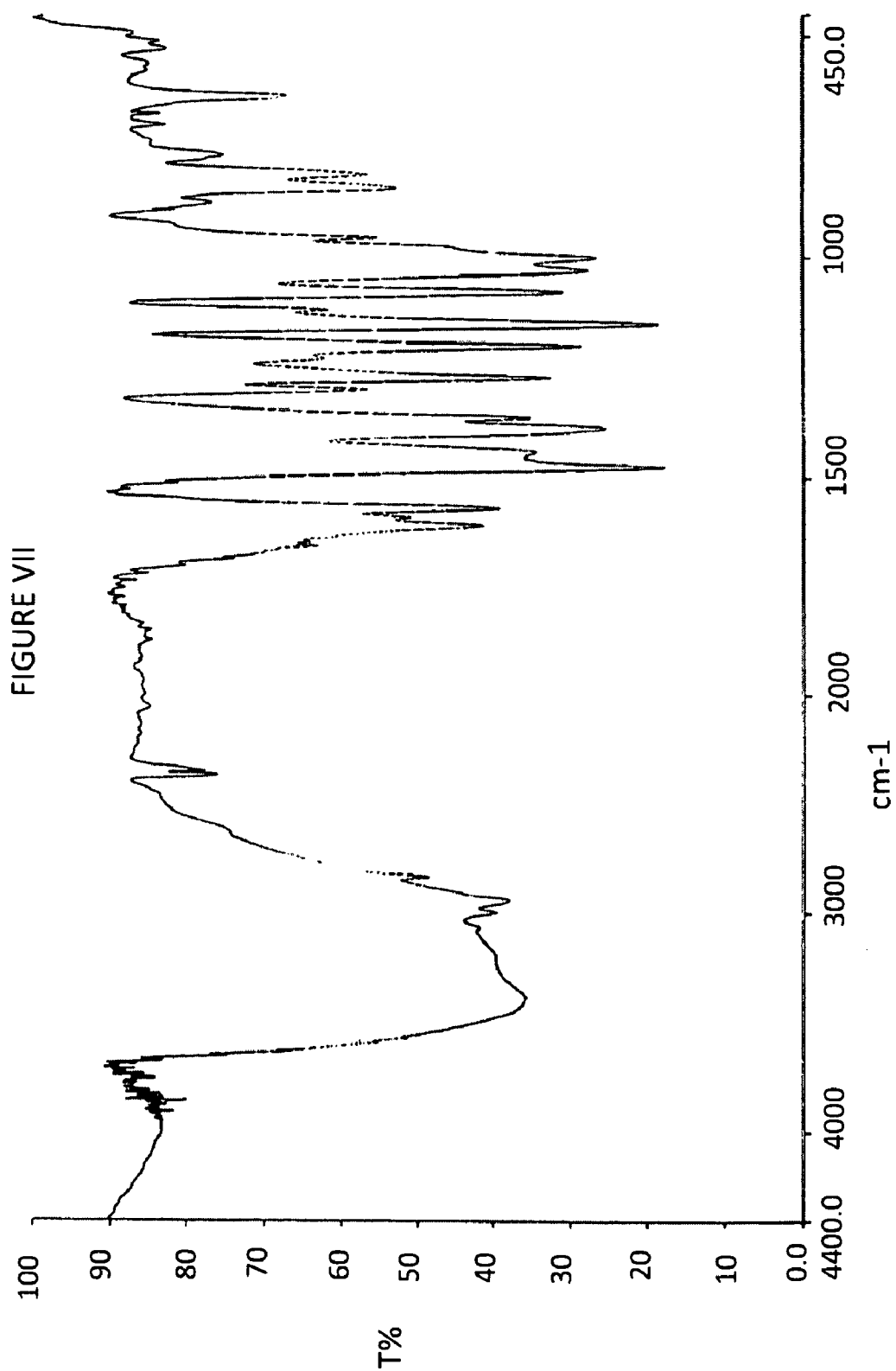
FIGURE VII

BARIUM SALT OF BENZIMIDAZOLE DERIVATIVE

CROSS REFERENCE TO RELATED APPLICATIONS

This application is a divisional application of U.S. patent application Ser. No. 10/555,628, now abandoned, which is a 371 of PCT/IB2004/001347, filed May 3, 2004, the contents of which are incorporated herein in its entirety.

FIELD OF THE INVENTION

A barium salt of the S-enantiomer of omeprazole which is (S)-5-methoxy-2-[[(4-methoxy-3,5-dimethyl-2-pyridinyl)-methyl]sulfinyl]-1H-benzimidazole is provided. Further, processes for preparing the barium salt, pharmaceutical compositions comprising the salt and a method of treatment or prevention of gastrointestinal ulcers comprising administration of the salt are provided.

BACKGROUND OF THE INVENTION

Omeprazole is a gastric acid secretion inhibitor, useful as an anti-ulcer agent. U.S. Pat. No. 5,714,504 describes alkaline salts of (S)-omeprazole, such as sodium, magnesium, lithium, potassium, calcium or tetraalkylammonium salts. However, only the preparation of sodium and magnesium salts of (S)-omeprazole has been exemplified, besides (S)-omeprazole freebase in this patent. The potassium salt of (S)-omeprazole has been described as prepared in WO 98/54171 and WO 00/44744. The commercially available magnesium salt of (S)-omeprazole is used for treating and preventing peptic ulcers, gastroesophageal reflux disease (GERD or heartburn), erosive esophagitis, other conditions involving excessive stomach acid production, and for treating bacterial infections caused by *helicobacter pylori*.

SUMMARY OF THE INVENTION

Herein is provided the barium salt of (S)-omeprazole, that is, (S)-omeprazole barium. Another aspect relates to (S)-omeprazole barium in a crystalline form. Yet another aspect relates to (S)-omeprazole barium in an amorphous form.

In yet another aspect, a process for preparing (S)-omeprazole barium is provided, which comprises contacting (S)-omeprazole freebase or its sodium/potassium salt with barium salt of an acid in a suitable solvent to form (S)-omeprazole barium, wherein the process is carried out in the presence of a base whenever (S)-omeprazole freebase is used. Alternatively, (S)-omeprazole barium may be prepared by a process which comprises contacting (S)-omeprazole freebase with barium hydroxide in a suitable solvent. Also, processes for preparing (S)-omeprazole barium in amorphous form are provided, which comprise concentrating a solution containing (S)-omeprazole barium to dryness or by spray drying the solution.

Further aspects include methods for treating or preventing gastrointestinal ulcers which comprise administering (S)-omeprazole barium, or a pharmaceutical composition that comprises (S)-omeprazole barium, along with pharmaceutically acceptable excipients.

BRIEF DESCRIPTION OF THE DRAWINGS

FIG. I illustrates the arrangement of FIGS. IA and IB with respect to each other for displaying an x-ray diffraction (XRD) pattern of the (S)-omeprazole barium in crystalline form prepared according to the process of Example 1.

FIGS. IA and IB are the x-ray diffraction patterns of FIG. I.

Figure 1A:
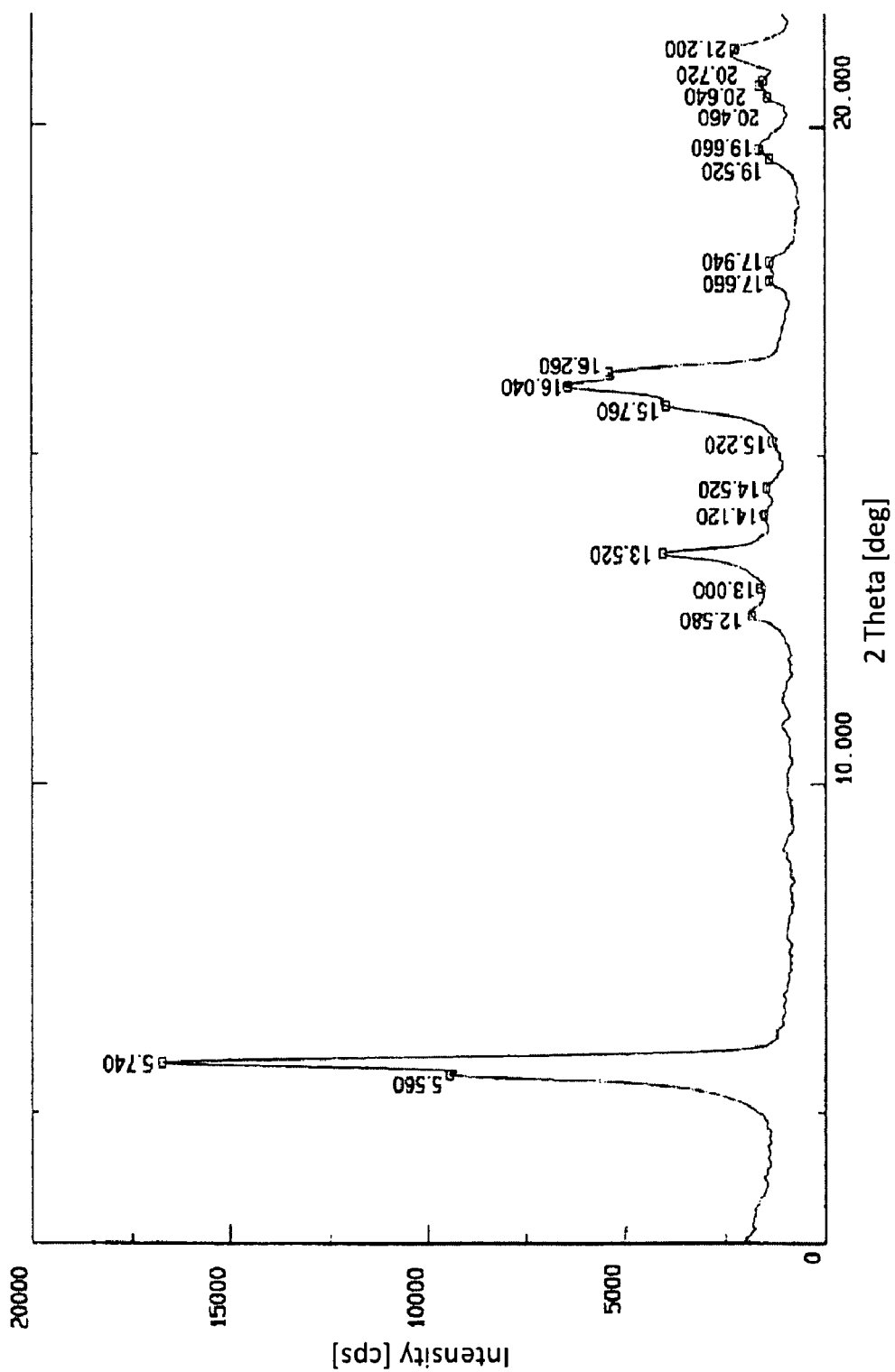
Figure 1B:
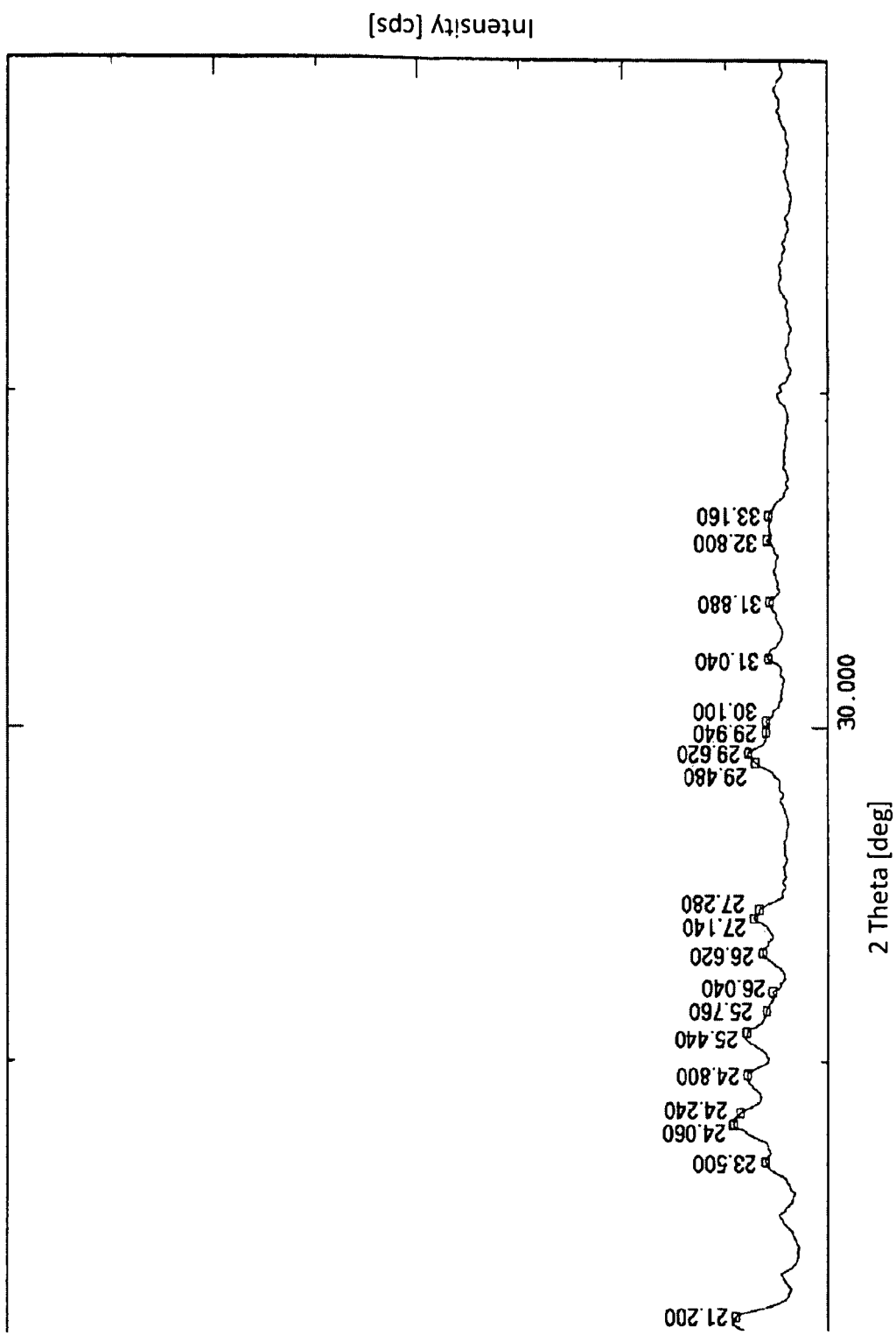

FIG. II is an infrared (IR) spectra of the (S)-omeprazole barium in crystalline form prepared according to the process of Example 1.

FIG. III illustrates the arrangement of FIGS. IIIA and IIIB with respect to each other for displaying an x-ray diffraction pattern of the (S)-omeprazole barium in crystalline form prepared according to the process of Example 2.

FIGS. IIIA and IIIB are the x-ray diffraction patterns of FIG. III.

FIG. IV is an x-ray diffraction pattern of the (S)-omeprazole barium in amorphous form prepared according to the process of Example 3.

FIG. V is an infrared spectra of the (S)-omeprazole barium in amorphous form prepared according to the process of Example 3.

FIG. VI is an x-ray diffraction pattern of the (S)-omeprazole barium prepared according to the process of Example 4.

FIG. VII is an infrared spectra of the (S)-omeprazole barium prepared according to the process of Example 4.

DETAILED DESCRIPTION OF THE INVENTION

The term "(S)-omeprazole barium" as used herein means any salt comprising (S)-omeprazole anions and barium cations. For instance, solid as well as dissolved forms are included, and so are crystalline and amorphous forms. (S)-omeprazole barium may exist in an anhydrous and/or solvent-free form or as a hydrate and/or a solvate.

The expression "(S)-omeprazole," as used herein, refers to an omeprazole-containing material which is substantially free of the R-enantiomer of omeprazole, for example, it has an enantiomeric excess of 80%, or for example an enantiomeric excess of 90%. In some particular embodiments, S-omeprazole is in enantiomeric excess of at least about 95%, or at least about 98%, or at least about 99.5%, or at least about 99.8%.

Further, the term "(S)-omeprazole barium," as used herein, encompasses stoichiometric as well as non-stoichiometric ratios of (S)-omeprazole anion and barium cation. The ratio of (S)-omeprazole to barium is not required to be 1:1 in order to be termed (S)-omeprazole barium. In a particular embodiment, (S)-omeprazole barium is formed as a salt having a 2:1 molar ratio between (S)-omeprazole anion and barium cation even when an excess of (S)-omeprazole or an excess of barium salt of an acid is used in the salt formation.

(S)-omeprazole barium obtained in both crystalline and amorphous forms is non-hygroscopic. An amorphous form may be advantageous in comparison with the crystalline form as it can be obtained in a finely powdered form with better solubility properties.

Examples of bases which may be used in the process for preparing (S)-omeprazole barium using (S)-omeprazole freebase include alkali metal hydroxides such as sodium hydroxide or potassium hydroxide, alkali metal carbonates such as sodium carbonate or potassium carbonate, alkali metal bicarbonates such as sodium bicarbonate, and ammonium hydroxide.

The barium salt of an acid to be used in the process can be the salt of any inorganic or organic acid. Examples of such salts include barium chloride, barium nitrate, barium sulphate, barium phosphate, barium carbonate, barium oxalate, barium acetate, barium lactate, barium succinate, barium citrate, and barium tartrate.

Examples of suitable solvents for carrying out the salt-forming processes include water, ketones such as acetone and methyl isobutyl ketone, alcohols such as methanol, ethanol and isopropanol, esters such as ethyl acetate and isopropyl acetate, chlorinated hydrocarbons such as methylene chloride and ethylene dichloride, cyclic ethers such as dioxan and tetrahydrofuran, nitriles such as acetonitrile, dipolar aprotic solvents such as dimethylsulfoxide and dimethylformamide, and mixtures thereof.

In water and methanol the reactants are more soluble than the (S)-omeprazole barium product. In this way, the salt-forming reaction is accompanied by spontaneous precipitation of the produced barium salt out of the solution. While such a precipitation in methanol gives crystalline (S)-omeprazole barium, in water the amorphous form is obtained.

Alternatively, the precipitation may be facilitated by reducing the volume of the solution and/or by adding an antisolvent, that is, a solvent in which the (S)-omeprazole barium is insoluble or sparingly soluble. The precipitation can also be induced by reducing the temperature of the solvent, especially if the initial temperature at contact is elevated.

Examples of anti solvents that may be added to precipitate out (S)-omeprazole barium include aliphatic hydrocarbons such as hexane, heptane, and octane; aromatic hydrocarbons such as xylene and toluene; lower alkyl ethers such as diethyl ether, and diisopropyl ether; and mixture(s) thereof.

The (S)-omeprazole freebase or its sodium/potassium salt to be used in the preparation processes can be obtained by methods known in the art including those described in U.S. Pat. Nos. 5,714,504, 5,948,789, and 6,162,816, and International Patent Applications WO 00/44744, WO 98/54171, and WO 92/08716. The starting (S)-omeprazole freebase or its sodium/potassium salts may be obtained as a solution directly, from a reaction in which S-omeprazole is formed, and used as such.

The precipitated barium salt may be isolated in a solid state by conventional methods such as filtration or centrifugation, optionally followed by washing and/or drying.

(S)-omeprazole barium may also be obtained in amorphous form by concentrating the solution of (S)-omeprazole barium to dryness or by spray drying the solution. Solutions of (S)-omeprazole barium may be obtained from the salt-forming reaction in a suitable solvent or by dissolving crystalline (S)-omeprazole barium in a suitable solvent.

(S)-omeprazole barium is a useful proton pump inhibitor and an antibacterial, and thus can be used to treat any condition that would be benefited by administration of a gastric acid secretion inhibitor. In particular, (S)-omeprazole barium can be used for the treatment or prophylaxis of gastric acid-related diseases and gastrointestinal inflammatory diseases in mammals and man, such as erosive or ulcerative gastroesophageal reflux disease (GERD), gastric ulcer, duodenal ulcer, reflux esophagitis, and gastritis.

Furthermore, it may be used for treatment of other gastrointestinal disorders where a gastric antisecretory effect is desirable, for example in patients on NSAID therapy, in patients with gastrinomas, and in patients with acute upper gastrointestinal bleeding. It may also be used in patients in intensive care situations, and pre- and post-operatively to prevent acid aspiration and stress ulceration. Further, (S)-omeprazole barium may be useful in the treatment of helicobacter infections and diseases related to these.

The salt can be administered as a component of a pharmaceutical composition. Accordingly, in a further aspect, there is provided a pharmaceutical composition that comprises (S)-omeprazole barium and pharmaceutically acceptable carriers, diluents or excipients and optionally other therapeutic ingredients. The salt may be conveniently formulated into tablets, capsules, suspensions, dispersions, injectables and other pharmaceutical forms. Any suitable route of administration may be employed for example, peroral or parental.

In the following section preferred embodiments are described by way of examples to illustrate the process of the invention. However, these are not intended in any way to limit the scope of the present invention. Variants of these examples would be evident to persons ordinarily skilled in the art.

EXAMPLES

General Experimental Details—Powder XRD

X-Ray Diffraction (XRD) patterns were taken with a diffractometer manufactured by Rigaku Corporation, specifically the model RU-H3R. The goniometer was a CN2155A3, and the X-Ray tube was equipped with Cu target anode. The settings for the divergence slits were 1 0, for the receiving slit 0.15 mm, and for the scatter slit 1 0. The operating power was 40 KV, 100 mA, the scanning speed was 2 deg/min step: 0.02 deg, and the wavelength was 1.5406 A.

General Experimental Details—FT-Infrared

Infrared spectra were taken with a Perkin Elmer, 16 PC, with scan parameters of 16 scans, 4.0 $cm^{-1}$ according to the USP 25, general test methods, page 1920. Infrared absorption spectra were obtained by the potassium bromide pellet method.

General Experimental Details—Differential Scanning Calorimetry

Differential Scanning Calorimetry was done by the model DSC821 e, manufactured by Mettler Toledo, with sample weights of 3-5 mg, and the sample temperature range of 25-100° C., heating rate of 1° C./min, nitrogen flow of 80.0 mL/min, with one hole in the crucible.

Example 1

A First Preparation of (S)-omeprazole barium in Crystalline Form (S)-omeprazole free base (5 g) was added to methanol (25 ml) and stirred at 25-30° C. Barium hydroxide (4.6 g) dissolved in methanol (40 ml) was slowly added to the above solution in 10 minutes at 25-30° C. The reaction mixture was further stirred for 1 to 2 hours, the obtained solid was filtered and washed with methanol. The product was air dried at 40 to 45° C. for 8 to 10 hours to get (S)-omeprazole barium (5.2 g).

HPLC Purity=98.56%, Chiral Purity by HPLC=99.89%. MC % w/w by KF=4.12%. XRD, IR spectra are as shown in FIGS. I and II respectively, as shown in the accompanying drawings.

Example 2

Potassium salt of (S)-omeprazole (10.0 g) was stirred in water (80 ml) and methylene chloride (80 ml). The suspension was cooled to 10 to 15° C. and dilute hydrochloric acid was added to adjust pH to 7.0 to 8.5. The reaction mixture was stirred for 5 minutes. The organic layer was separated and washed with water. The solvent was recovered under reduced pressure at 30-35° C. to obtain an oily residue. Methanol (40 ml) was added, and the mixture stirred for 10 to 15 minutes.

Barium hydroxide (9.0 g) dissolved in methanol (90 ml) was slowly added to the above solution in 10 minutes at 25-30° C. The reaction mixture was further stirred for 1 to 2 hours. The solid obtained was filtered, washed with methanol and air dried at 40 to 45° C. for 8 to 10 hours to get (S)-omeprazole barium (8.1 g).

HPLC Purity=97.98%, Chiral Purity by HPLC=100%. MC % w/w by KF=7.46%. XRD spectrum is as shown in FIG. III, as shown in the accompanying drawings. IR spectrum is similar to that shown in FIG. II for Example I.

Example 3

Preparation of (S)-omeprazole barium in Amorphous Form (S)-omeprazole free base (5 g) was added to acetone (60 ml) and stirred at 25-30° C. Barium hydroxide octahydrate (4.6) and water (15 ml) were then added to the above mixture at 25-30° C. The reaction mixture was further stirred for 4 to 5 hours, and then filtered to remove suspended solid material. The solvent was recovered under reduced pressure to obtain the product as a foam. The product was dried at 40 to 45° C. under reduced pressure for 2 to 3 hours to get (S)-omeprazole barium (4.2 g).

HPLC Purity=99.43%, Chiral Purity by HPLC=99.99%, MC % w/w by KF=2.66%. XRD, IR spectra are as shown in FIGS. IV and V respectively, as shown in the accompanying drawings.

Example 4

Potassium salt of (S)-omeprazole (5 g) was dissolved in water (60 ml) at 25-30° C. to get a clear solution. Barium chloride dihydrate (3.2 g) dissolved in water (10 ml) was slowly added to the above solution in 10 minutes at 25-30° C. The reaction mixture was further stirred for 1 to 2 hours, the obtained solid was filtered and washed with water. The product was air dried at 40 to 45° C. for 8 to 10 hours to get (S)-omeprazole barium (3.4 g), MC % w/w by KF=0.10%.

XRD, IR spectra are as shown in FIGS. VI and VII respectively as shown in the accompanying drawings.

Example 5

Crystalline (S)-omeprazole barium (3 g) was added to acetone (60 ml) and stirred at 25-30° C. The solution was then filtered to remove any suspended solid material. The solvent was recovered under reduced pressure at 40 to 45° C. to obtain the product as a foam. The product was dried at 40 to 45° C. under reduced pressure for 2 to 3 hours to get (S)-omeprazole barium (2.5 g). HPLC Purity=99.27%, MC % w/w by KF=2.10%.

XRD, IR spectra are similar to those shown in FIGS. IV and V respectively for Example 3.

Example 6

Crystalline (S)-omeprazole barium (5.0 g) was added to acetone (100 ml) and stirred at 25-30° C. The solution was then filtered to remove any suspended solid material and subjected to spray drying under nitrogen atmosphere (inlet temperature 50 to 60° C. and outlet temperature 40 to 45° C.). The product so obtained was dried at 40 to 45° C. under reduced pressure for 2 to 3 hours to get (S)-omeprazole barium (3.0 g). MC % w/w by KF=1.2%.

XRD, IR spectra are similar to those shown in FIGS. IV and V respectively for Example 3.

While the present invention has been described in terms of its specific embodiments, certain modifications and equivalents will be apparent to those skilled in the art and are intended to be included within the scope of the present invention.

We claim:

1. A process for the preparation of (S)-omeprazole barium comprising the step of contacting (S)-omeprazole freebase, or its salt, with a barium containing compound that is capable of forming the barium salt (S)-omeprazole in a solvent, provided that a base is used when (s)-omeprazole base is used as the starting material, wherein the solvent comprises water, ketones, alcohols, esters, cyclic ethers, chlorinated hydrocarbons, nitriles, dipolar aprotic solvents, and mixtures thereof.

2. The process according to claim 1, wherein the barium containing compound is the barium salt of an inorganic acid.

3. The process according to claim 2, wherein the barium salt is selected from the group consisting of barium chloride, barium nitrate, barium phosphate, barium carbonate, and barium sulfate.

4. The process according to claim 1, wherein the barium salt of an organic acid is used.

5. The process according to claim 4, wherein the barium salt is selected from the group consisting of barium oxalate, barium acetate, barium lactate, barium succinate, barium citrate, and barium tartrate.

6. The process according to claim 1, wherein the base is selected from the group consisting of alkali metal hydroxides, alkali metal carbonates, alkali metal bicarbonates and ammonium hydroxide.

7. The process according to claim 6, wherein the base is selected from the group consisting of sodium hydroxide, potassium hydroxide, sodium carbonate, potassium carbonate, and sodium bicarbonate.

8. The process according to claim 1, wherein the solvent is selected from the group consisting of water, acetone, methanol and mixtures thereof.

9. The process according to claim 1, wherein the product obtained is crystalline (S)-omeprazole barium.

10. The process according to claim 1, which further comprises removing the solvent by vacuum distillation or spray drying.

* * * * *